United States Patent
Murphy et al.

[11] Patent Number: 6,125,164
[45] Date of Patent: Sep. 26, 2000

[54] HIGH-SPEED INTER-MODALITY IMAGE REGISTRATION VIA ITERATIVE FEATURE MATCHING

[75] Inventors: Martin J. Murphy, San Carlos; Richard S. Cox, deceased, late of San Francisco, both of Calif., by Randall Cox, legal representative

[73] Assignee: The Board of Trustees of the Leland Stanford Junior University, Palo Alto, Calif.

[21] Appl. No.: 09/198,187

[22] Filed: Nov. 23, 1998

Related U.S. Application Data

[63] Continuation-in-part of application No. 08/890,776, Jul. 11, 1997.

[51] Int. Cl.[7] .................................................. A61N 5/01
[52] U.S. Cl. ................................................. 378/65; 606/33
[58] Field of Search .............................. 378/65; 606/33; 604/19, 20

[56] References Cited

U.S. PATENT DOCUMENTS

5,859,891  1/1999  Hibbard ........................... 378/62
5,901,199  5/1999  Murphy et al. .................... 378/65

*Primary Examiner*—David V. Bruce
*Attorney, Agent, or Firm*—Lumen Intellectual Property Services

[57] ABSTRACT

This invention describes a system and method for aligning radiation therapy beams with a treatment target of a patient. Diagnostic computer tomography scanning is used to map the treatment target in the patient's anatomy and to aid physicians in deciding where to aim the radiation therapy beams. Digitally reconstructed radiographs are generated from an intermediate 3-D image produced from the CT scans. These DRRs are compared with x-ray images taken of the treatment target's position taken at the time of treatment. A transformation equation is used to compare the DRRs and the x-ray images. A minimization equation is used to determine the similarity between the two sets of images. If the difference between the two sets fall below a determined minimum value, then the position of the treatment target is deemed correct and the radiation therapy begins. If the difference does not fall below the determined minimum value, then either the radiation beams or the treatment target is adjusted and the process is repeated. This procedure may be used many times in the course of a single treatment session, depending on the movement of the patient.

22 Claims, 11 Drawing Sheets

Fits of the deduced versus actual phantom position
data to straight lines and standard deviations σ

| single component motion | two parameter fit | | one parameter fit | |
|---|---|---|---|---|
| | slope | σ | slope | σ |
| x | 1.05±0.05 | 0.5 mm | 1.00 | 0.6 |
| y | 0.73±0.07 | 0.5 mm | 1.00 | 1.0 |
| α | 1.03±0.04 | 0.67° | 1.00 | 0.67° |
| β | 0.93±0.05 | 0.82° | 1.00 | 0.92° |
| γ | 0.77±0.05 | 0.54° | 1.00 | 1.37° |
| composite motion | | | | |
| α | 0.89±0.03 | 0.71° | 1.00 | 1.01° |
| β | 0.91±0.05 | 0.79° | 1.00 | 0.85° |

HIGH-SPEED INTER-MODALITY IMAGE REGISTRATION VIA ITERATIVE FEATURE MATCHING

RELATED APPLICATION INFORMATION

This application is a continuation-in-part of U.S. application Ser. No. 08/890,776 filed Jul. 11, 1997, which is herein incorporated by reference.

FIELD OF THE INVENTION

This invention relates to the field of medical imaging. More particularly, it relates to a real-time method of positioning therapeutic radiation beams with respect to a target area within a patient and a system for doing the same.

BACKGROUND OF THE INVENTION

Radiation therapy is often used to treat cancerous tumors within a patient's body. An early diagnostic session is conducted where the physician uses an imaging technique, such as computed tomography (CT) scanning or magnetic resonance imaging (MRI) to study the target area. He or she then decides the ideal placement and volume of the radiation beam(s) with respect to the target area. During the actual treatment, the radiation beams are focused directly at the target area, using the diagnostic studies as a position reference. Precise positioning of the radiation beams insures that most of the radiation contacts the target cells, while also insuring that the healthy cells surrounding the target cells are not affected. Unfortunately, it is often difficult to be certain that radiation beams are optimally positioned with respect to target cells. Often, a smaller total dose of radiation must be used in order to reduce the possibility of damage to healthy cells. The consequence, however, is that the radiation treatment becomes less effective.

In addition, radiotherapy often requires a patient to return for treatment over the course of several days. Repositioning a patient precisely each time can be time-consuming and frustrating.

Over the past decade, many methods have been devised to improve the alignment of radiation beams with the target area of a patient. An early method involves a rigid frame to physically hold in place the part of the patient's body to be treated. In one embodiment for treatment of target areas within a patient's skull, the frame is attached to a floorstand mounted in a Linac (linear accelerator) floor turret. This method is considered generally reliable and accurate, as it fixes the target area rather precisely with respect to the radiation beams. Unfortunately, due to the nature of the frame, it also greatly limits accessibility to the patient's skull. Target areas may be located in the skull where the Linac radiation beams cannot reach. In addition, it is extremely uncomfortable for the patient, who must remain in an awkward position for long periods of time.

Another method involves invasive techniques. U.S. Pat. No. 5,097,839 by Allen describes fiducial implants attached in a pattern to a patient's skull bones, underneath the skin. These implants are then used as fixed references when aligning radiation beams with the target area. These implants are an improvement over rigid frames in that they allow all target areas within a skull to be reached. However, because inserting the fiducial implants into the patient is a surgical procedure itself, the patient must often wait for several days until the radiation treatment. During this time, the target area may grow or otherwise change in shape, rendering inaccurate the early diagnostic analyses taken when the fiducial implants were put in place. In addition, the implants are often disfiguring and painful to the patient.

Another type of invasive technique involves placing tattoos on the patient's skin where the radiation beams are to enter. Although this is less intrusive than the fiducial implants, it has many of the same problems, such as the patient having to wait several days from the time of the tattoo procedure until the radiation treatment, thus giving time for the target area to grow or change shape. In addition, given the nature of tattoos, it is possible they may also change shape.

More recently, non-invasive, non-disfiguring alignment systems have been developed. These typically use signal processing to convert the CT or MRI data of the position of the patient in the diagnostic setting to the position of the patient in the treatment setting. Many of these systems require a large amount of preprocessing, whereby data generated from the diagnostic scan is gathered and manipulated until it is usable in the treatment setting. The preprocessing step can take several days. During treatment, real time images are compared with the preprocessing data and the patient or the radiation therapy beams are adjusted accordingly. Oftentimes, manual adjustment is necessary. Three degrees of freedom, corresponding to one plane, are typically allowed. The patient has greater freedom of movement than in the previously described techniques, but his movement is still confined. These systems are generally accurate, and painless for the patient.

U.S. Pat. No. 5,295,200 by Boyer et al. describes a method of aligning radiation therapy beams using the Fast Fourier Transform (FFT) to compare the position of diagnostic images with the position of treatment images. In this invention, a large amount of complex data must be gathered and processed prior to treatment. Reference images collected during the diagnostic study are later used to position the patient during treatment.

U.S. Pat. No. 5,531,520 by Grimson et al. describes a method of image registration that takes into consideration patient movement within six degrees of freedom. It employs lasers to determine patient position and as such is confined to surface images. Thus, treatment beams must be based relative to tattoos or other markers on a patient's skin, which have the problems mentioned above.

These existing alignment methods require an extensive amount of time to process complex diagnostic data, usually restrict accuracy to three degrees of freedom, limit patient movement, and make adjustment of either the treatment beams or the patient difficult. In addition, they are unable to generate instant reference images with which to compare the present position of a patient. They also require manual operations to supplement automatic procedures.

OBJECTS AND ADVANTAGES OF THE INVENTION

Accordingly, it is a primary object of the present invention to provide a wholly automatic system and method of aligning radiation therapy beams with the treatment target of a patient. It is another object of the invention to provide such a method by making use of radiographic techniques. Yet another object of the invention is to decrease the time required for the preprocessing step, as well as reduce the complexity of data manipulation. A further object of this invention is to generate instant reference images derived from the diagnostic study with which to compare the present position of the treatment target. Another object of the invention is to allow a patient to move around freely during treatment. A sixth object of the invention is to measure patient movement within six degrees of freedom. A seventh object of the invention is to provide continuous adjustment of radiation therapy beams to improve precision during the course of treatment. A final object of this invention is to accommodate both diagnostic imaging and treatment of a patient in the same day.

SUMMARY OF THE INVENTION

These objects and advantages are attained by the present invention. This method begins with a diagnostic computed tomographic (CT) scan of the treatment target of a patient. The information from the CT scan is used to generate an intermediate 3-D image. This intermediate 3-D image will eventually be moved or rotated to mimic the position of the treatment target. During treatment, the position of the treatment target in relation to the radiation therapy beams is recorded using at least two x-ray cameras. Thus, both translational and rotational information is received. The treatment images are then processed to produce a feature vector, which is specific for those set of images and thus the position of the treatment target.

Using the intermediate 3-D image generated during the diagnostic stage, at least two digitally reconstructed radiographs (DRRs) are produced. These radiographs are wholly artificial constructs that are judged to be similar to the treatment images. These DRRs are also processed to produce a feature vector. The difference between the two feature vectors is then calculated using a mathematical equation, for example chi squared. If the difference falls below a minimum allowable value, then the position of the treatment target is deemed accurate enough to begin radiation therapy. However, if the difference does not fall below the minimum allowable value, then the intermediate 3-D image is iteratively moved within six degrees of freedom until successive DRRs produce an acceptable minimum difference with respect to the treatment images. Data from the repositioned intermediate 3-D image is used to adjust either the patient or the radiation therapy beams, thus achieving accurate alignment of the radiation beams and the treatment target.

DETAILED DESCRIPTION

Figure 1:
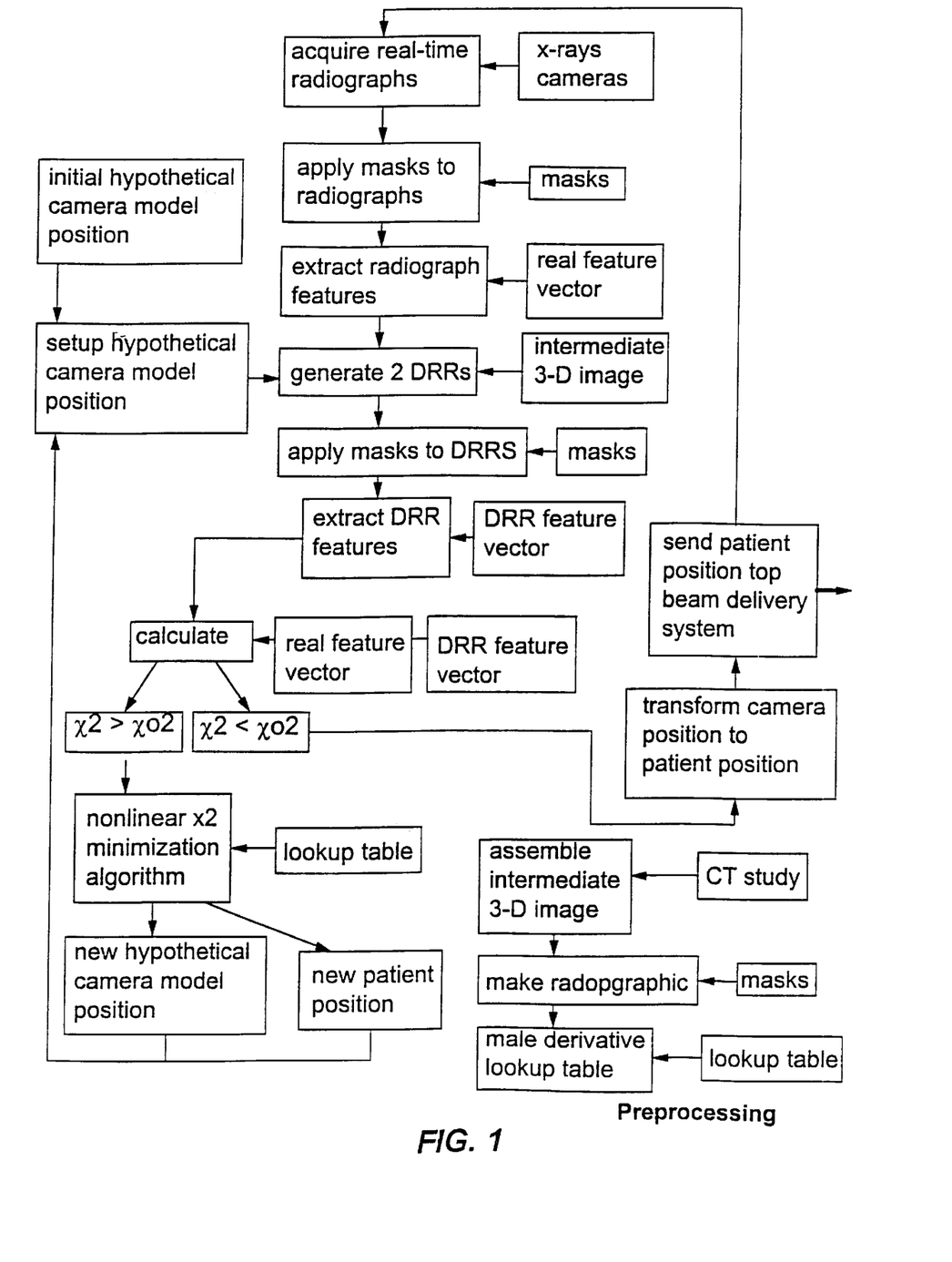
FIG. 1 is a flow chart illustrating the operation of the invention.
Figure 2:
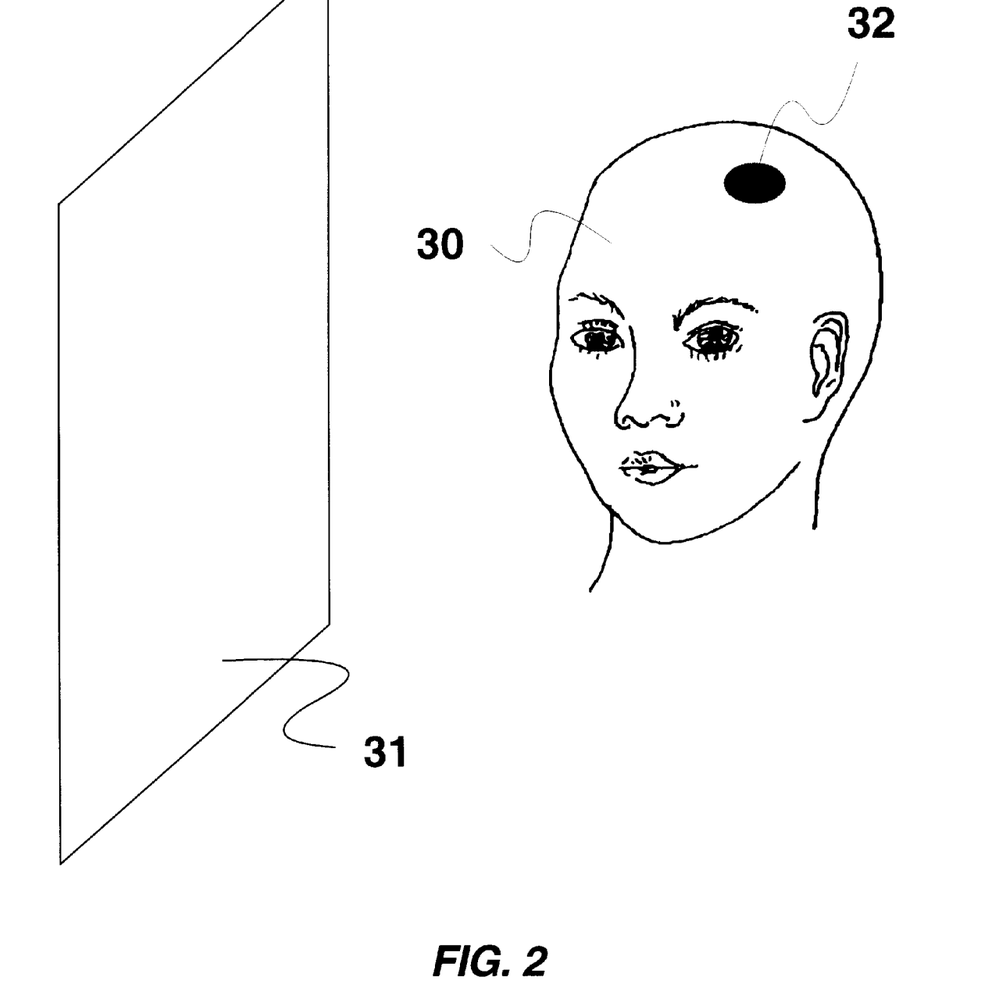
FIG. 2 shows a radiograph produced from a patient with a brain tumor.
Figure 3:
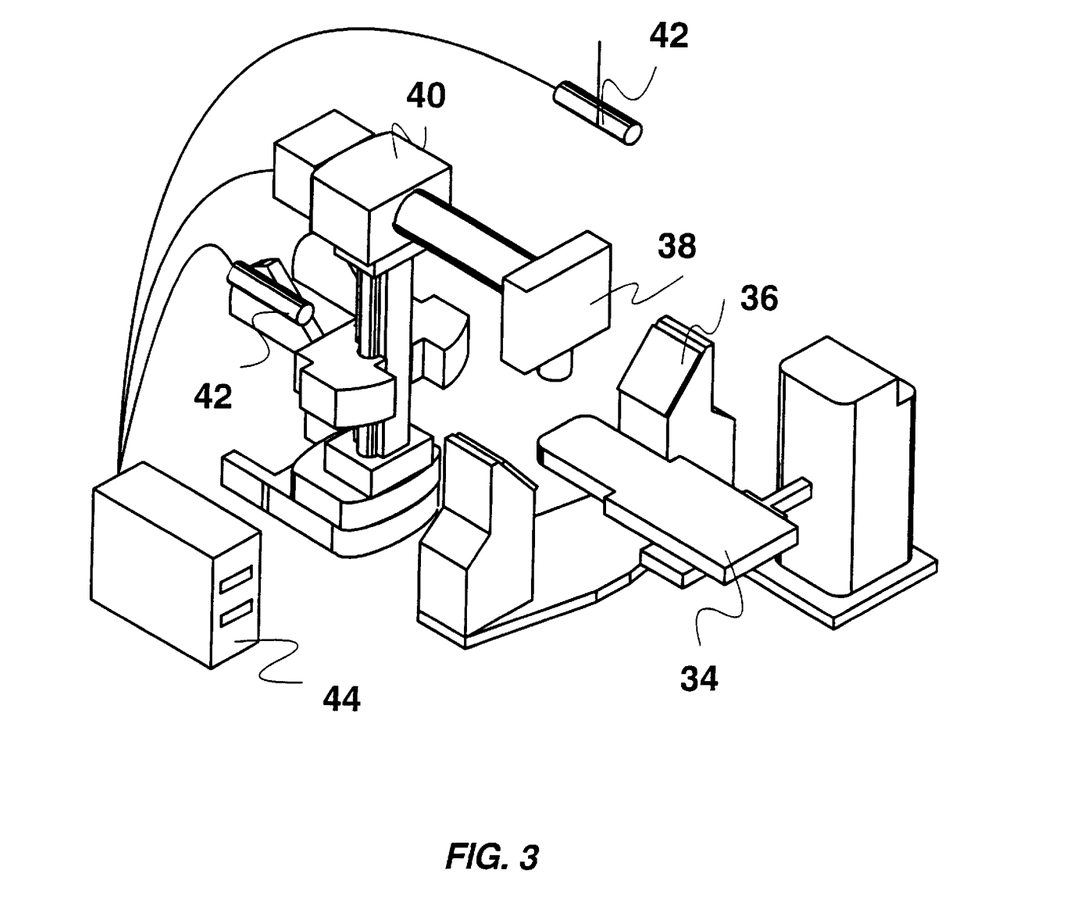
FIG. 3 is a diagram of the apparatus, consisting of a Cyberknife connected to a computer system.
Figure 6:
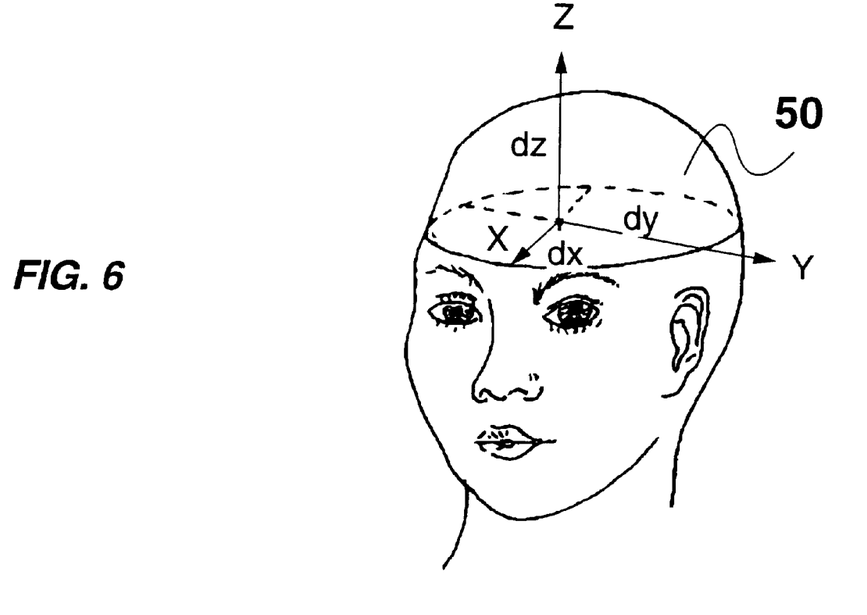
FIG. 6 is a diagram showing the three translational degrees of freedom in the preferred embodiment.
Figure 7:
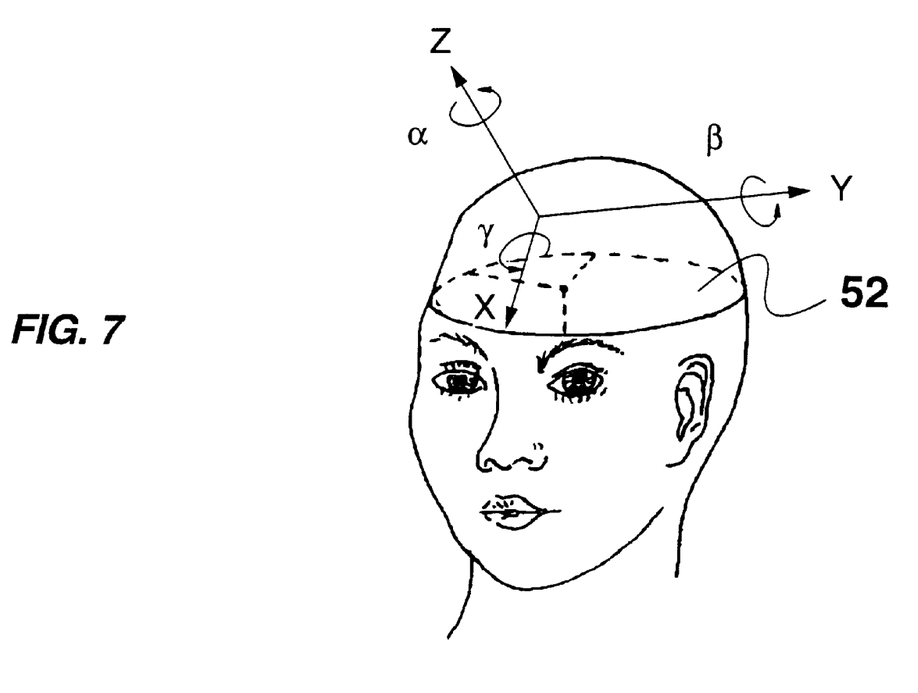
FIG. 7 is a diagram showing the three rotational degrees of freedom in the preferred embodiment.
Figure 8:
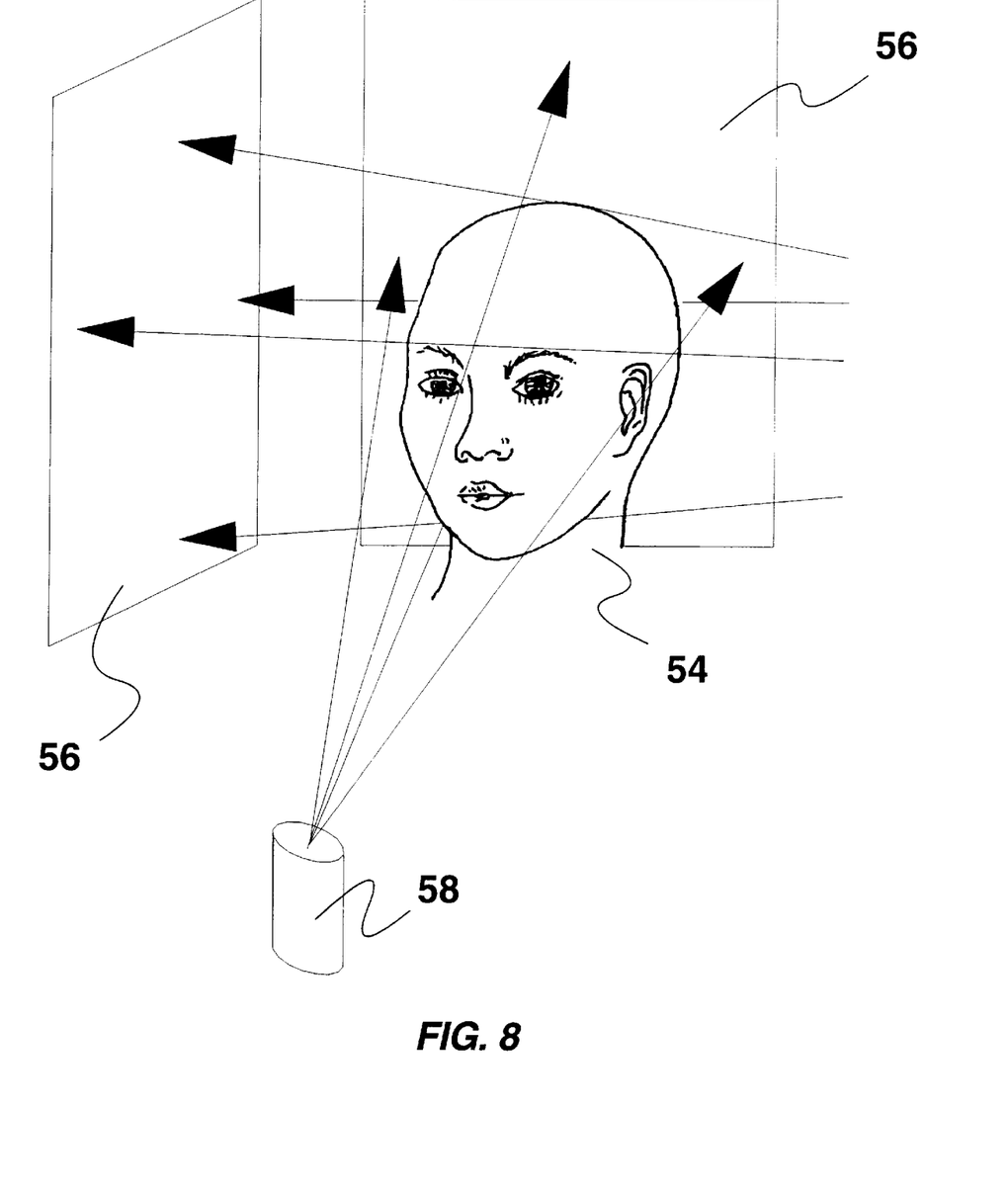
FIG. 8 is a diagram illustrating the projection geometry for generating two digitally reconstructed radiographs (DRRs) from the intermediate 3-D image using a hypothetical camera model.

The method of the invention is described for use with the Cyberknife, as shown in FIG. 3, and a patient 30 with a brain tumor 32, as shown in FIG. 2. Please note the method of this invention is not confined for use with the Cyberknife. In the preprocessing step, patient 30 undergoes a computed tomography (CT) scan of his skull. The CT scans are used to assemble an intermediate 3-D image 54, as shown in FIG. 8. Intermediate 3-D image 54 can be moved and rotated along both translational axes 50 and rotational axes 52 in the diagnostic coordinate system, as shown in FIGS. 6 and 7. In this representation, translational axes 50 are represented by dx, dy, and dz, while the rotational axes 52 are represented by $\alpha$, $\beta$, $\gamma$. Thus up to six degrees of freedom of movement are allowed. Intermediate 3-D image 54 may consist solely of computer script within a computer or system of computers 44 or it may be visualized on a monitor.

Figure 9:
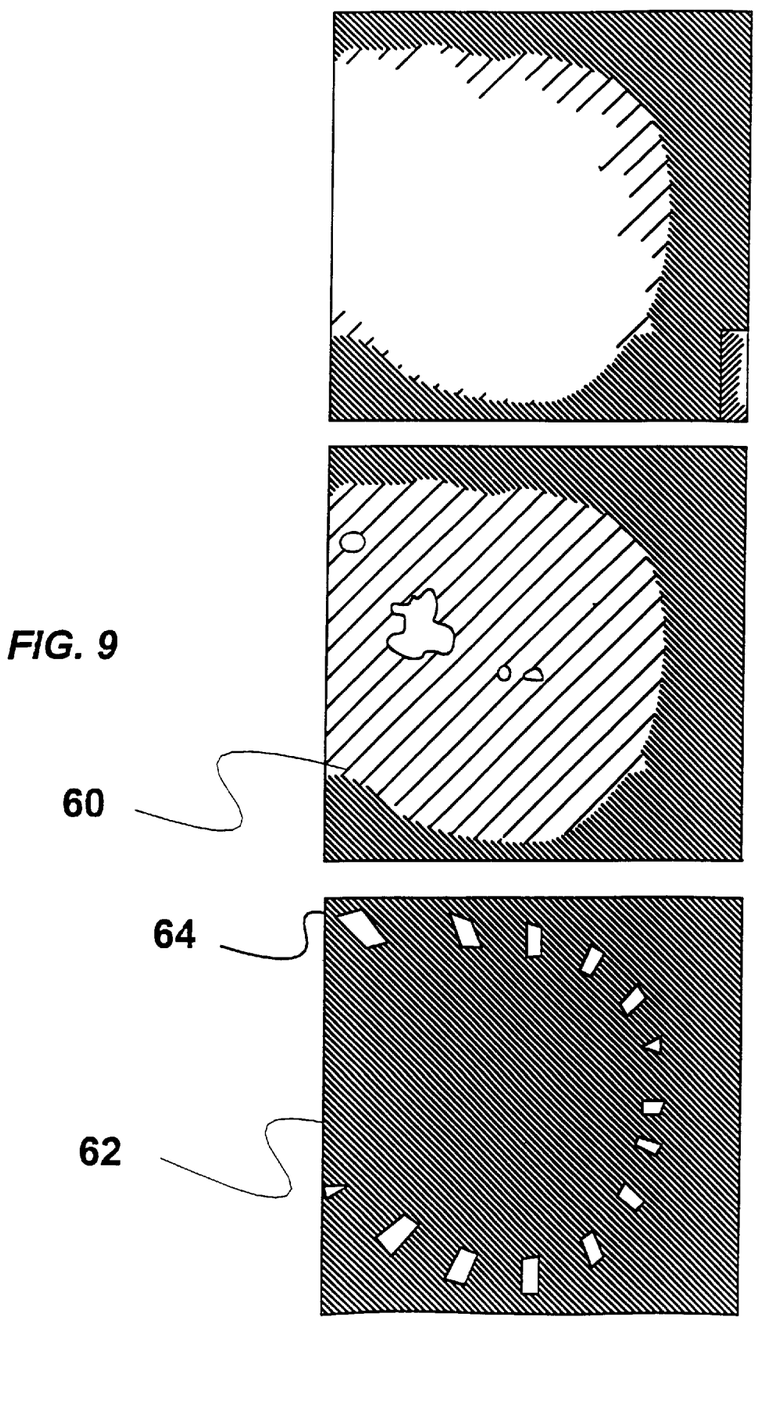
FIG. 9 shows a representation of a fluoroscopic image of an anthropomorphic phantom, a DRR of said anthropomorphic phantom, and a DRR marked with key pixels to locate anatomical edge features.

In the preferred embodiment, intermediate 3-D image 54 is used to generate a set of at least two digitally reconstructed radiographs (DRRs) 56, as shown in FIG. 8. DRRs 56 are artificial 2-D images that show how intermediate 3-D image 54 would appear from different angles using a hypothetical camera model 58. Each DRR 56 of a set represents one hypothetical camera angle. These DRRs 56 can then be masked to isolate key pixels associated with anatomical edge features 64, as shown in FIG. 9 where hatched regions and un-hatched regions represent regions of pixels with different image densities. Where a complete image 60 would have 40,000 pixels, for example, a masked image 62 typically has 1,000 to 4,000 key pixels 64.

The set of masked DRRs 62 may then be used to generate a lookup table. The lookup table provides the first derivatives of said translational and rotational measurements of intermediate 3-D image 54. These calculations can be used later during treatment to match the actual patient images with intermediate 3-D image 54. The preprocessing procedure as described above requires about 20 seconds on a computer or computer systems 44 with 200 MHz processors.

Figure 4:
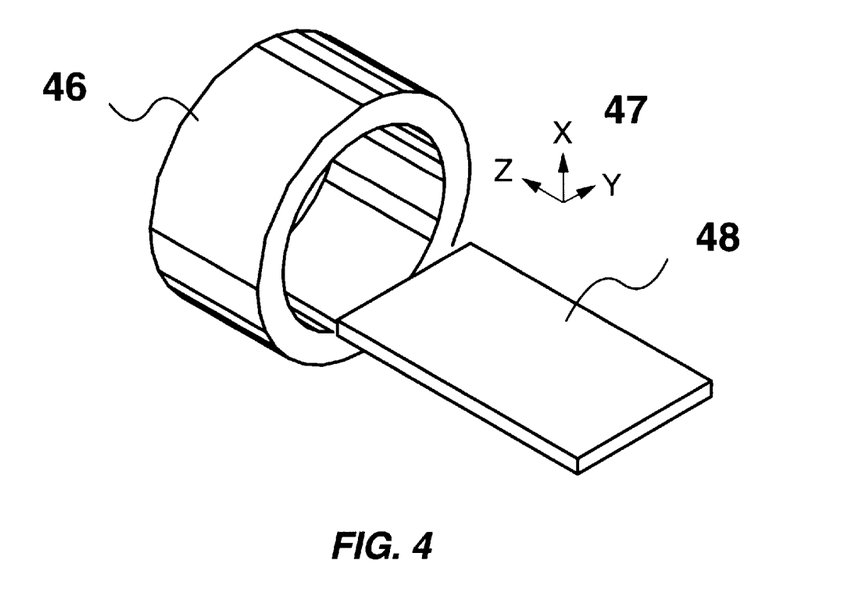
FIG. 4 is a diagram showing the diagnostic coordinate system.
Figure 5:
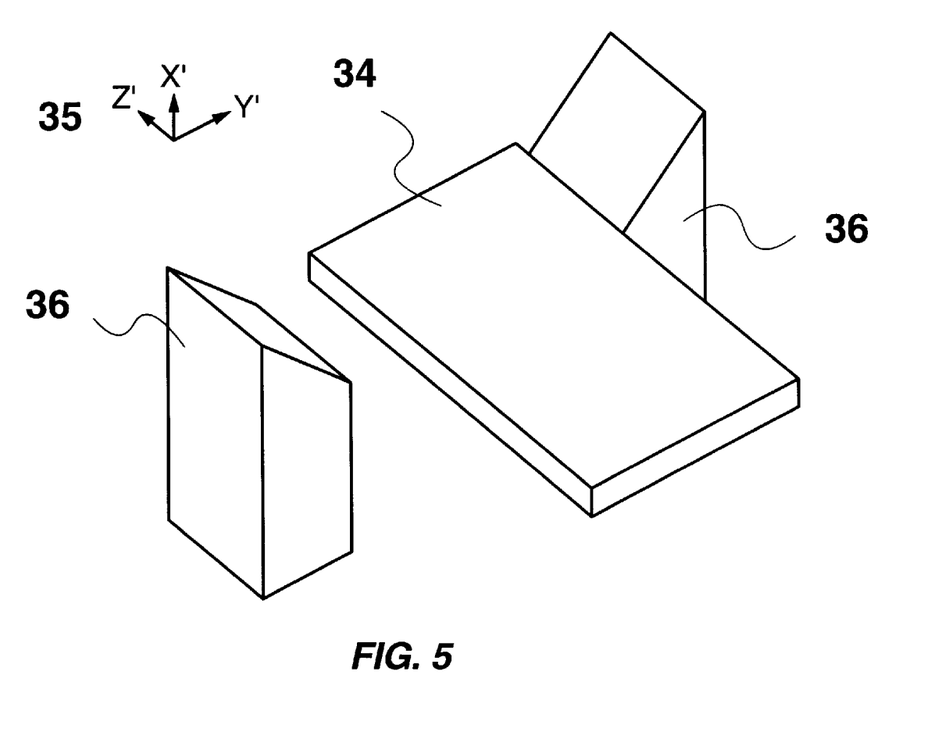
FIG. 5 is a diagram showing the treatment coordinate system.

During treatment, the patient is placed within the view of at least two radiographic cameras 42, in a position approximating his position during the diagnostic scan. The patient has complete freedom of movement, as all possible positions can be defined within six degrees of freedom using translational axes 50 and rotational axes 52, as shown in FIGS. 6 and 7. Translational axes 50 and rotational axes 52 of the treatment coordinate system, as shown in FIG. 5, are defined in the same manner as translational axes 50 and rotational axes 52 of the diagnostic coordinate system, as shown in FIG. 4. (On the Cyberknife, patient 30 has two x-ray cameras 42 and screens 36, which produce real-time radiographs 31 of treatment target 32). These real-time radiographs 31 may then be processed in the same manner as DRRs 56. Real-time radiographs 31 are masked to isolate key pixels associated with anatomical edge features 64. Masked real-time radiographs 31 are used to produce a first feature vector, which specifically identifies the position and orientation of treatment target 32 within the treatment coordinate system, as shown in FIG. 5, at the time real-time radiographs 31 were taken.

Next, intermediate 3-D image 54 is manipulated until its position emulates the position and orientation of treatment target 32. New DRRs 56 are then generated from intermediate 3-D image 54, as shown in FIG. 8. These DRRs 56 are masked to isolate the same key pixels 64 as in real-time radiographs 31 and processed to produce a second feature vector, which specifically identifies the position and orientation of the treatment target of intermediate 3-D image 54 within the diagnostic coordinate system, as shown in FIG. 4.

The two feature vectors are then compared using a mathematical equation, for example the chi squared statistic. If treatment target 32 of patient 30 is positioned in the treatment coordinate system, as shown in FIG. 5, in precisely the same way as intermediate 3-D image 54 is positioned in the diagnostic coordinate system, as shown in FIG. 4, then the difference between the two feature vectors, or $\chi^2$, will be less than a designated minimum value. The system has then completed its determination of treatment target 32 position and orientation. This information is passed on to the beam delivery system 40 (e.g. the Cyberknife) and the radiation therapy beams 38 are allowed to operate.

If, however, treatment target 32 is not positioned in the same position and orientation as in the diagnostic coordinate system, the two feature vectors will exhibit $\chi^2$ greater than the designated minimum value. In this case, the system moves to the $\chi^2$ minimization step. The $\chi^2$ minimization process searches for a match between real-time radiographs 31 and DRRs 56 by iteratively varying the position and orientation of intermediate 3-D image 54 with respect to hypothetical camera model 56. For a radiographic imaging system consisting of at least two CCD fluoroscopes, hypothetical camera model 58 is a multi-parameter function which maps the CCD image plane to the fluoroscope screen, and the fluoroscope screen to the treatment coordinate system, as shown in FIG. 5. It accounts for magnification, relative positioning of the two fluoroscopes in the treatment room coordinate system, tilt of the image planes with respect to the fluoroscope screens (in three independent directions), and radial (spherical) distortion of the lens system. Radial distortion is modeled by the factor:

$$x'=x/(1+\lambda R^2)$$
$$y'=y/(1+\lambda R^2)$$

where x and y are the pixel coordinates on the CCD image plane, x' and y' are the corresponding coordinates on the fluoroscope screen, $R^2=(x^2+y^2)$, and $\lambda$ is a free parameter that is determined when hypothetical camera model 58 is calibrated.

The parameters of hypothetical camera model 58 are determined by fitting DRRs 56 of a calibration phantom to actual radiographs 31 of the phantom, using the same $\chi^2$ minimization process as for patient position measurements. The residual errors in this calibration-fitting process are spatially random and on the order of the image pixel dimensions, indicating that there is no significant distortion left unaccounted for by the model.

The various positions of the treatment target are emulated in DRRs 56 by changing the point of view of hypothetical camera model 58 with respect to intermediate 3-D image 54. This movement is achieved by use of the lookup table created in the preprocessing step, as described above. The process continues until the difference between the two feature vectors falls below the designated minimum value. At this point, the new coordinates of hypothetical camera model 58 in the diagnostic coordinate system are translated into coordinates for the treatment coordinate system. This information is sent to beam delivery system 40 and radiation therapy beams 38 are realigned. It is also possible to reposition patient 30. Radiation therapy beams 38 are then allowed to operate.

Translation of intermediate 3-D image 54 rotation geometry into the treatment target geometry is accomplished most effectively via an Eulerian (body-fixed) rotation convention. The Eulerian convention properly represents the fact that patient's rotational axes 52 are fixed in anatomy and not in an external reference frame. On the other hand, mechanical beam and patient alignment systems can measure angles in the space-fixed ($\alpha$, $\beta$, $\gamma$) convention illustrated in FIG. 10. To relate space-fixed rotations in ($\alpha$, $\beta$, $\gamma$) with the rotations deduced by the image registration algorithm requires that the Eulerian DRR rotations be inverted to correspond to rotations of the object rather than hypothetical camera model 58 (bearing in mind that sequential rotations do not commute) and then transformed to the space-fixed rotation convention. This transformation is summarized below.

Let us designate treatment target 32 in the skull of patient 30 by the vector X in the space-fixed camera coordinate system. When treatment target 32 rotates through the angles ($\alpha$, $\beta$, $\gamma$), its coordinates in the fixed frame become $$X''=[\Lambda\gamma][\Lambda\beta][\Lambda\alpha]X$$

where the rotation matrices are:

$$[\Lambda_\gamma] = \begin{matrix} 1 & 0 & 0 \\ 0 & \cos\alpha & \sin\alpha \\ 0 & -\sin\alpha & \cos\alpha \end{matrix}$$

$$[\Lambda_\beta] = \begin{matrix} \cos\beta & 0 & \sin\beta \\ 0 & 1 & 0 \\ -\sin\beta & 0 & \cos\beta \end{matrix}$$

$$[\Lambda_\alpha] = \begin{matrix} \cos\gamma & -\sin\gamma & 0 \\ \sin\gamma & \cos\gamma & 0 \\ 0 & 0 & 1 \end{matrix}$$

This convention locates points in the anatomy of patient 30 in the fixed treatment coordinate frame that beam delivery system 40 refers to in directing treatment beam 38.

The DRR ray-tracing process works most effectively in a coordinate system fixed to the image plane in hypothetical camera model 58. The image plane of hypothetical camera model 58 is positioned within the diagnostic coordinate system, relative to intermediate 3-D image 54, through the three Eulerian rotations ($\phi_0$, $\theta_0$, $\psi_0$). Rotations of the patient's anatomy with respect to x-ray cameras 42 can then be represented in the DRR process by moving the image plane of hypothetical camera model 58 through ($\phi_0$, $\theta_0$, $\chi_0$) to the perturbed orientation ($\phi_0+d\phi$, $\theta_0+d\theta$, $\psi_0+d\psi$). If a point in the patient's anatomy is located by the vector X' in the coordinate frame fixed to the image plane, then X and X' are related according to the transformation:

$$X''=[\Lambda\phi][\Lambda\theta][\Lambda\psi]X$$

where the rotation matrices are:

$$[\Lambda_\phi] = \begin{matrix} 1 & 0 & 0 \\ 0 & \cos\phi & \sin\phi \\ 0 & -\sin\phi & \cos\phi \end{matrix}$$

$$[\Lambda_\theta] = \begin{matrix} \cos\theta & 0 & \sin\theta \\ 0 & 1 & 0 \\ -\sin\theta & 0 & \cos\theta \end{matrix}$$

$$[\Lambda_\psi] = \begin{matrix} \cos\psi & -\sin\psi & 0 \\ \sin\psi & \cos\psi & 0 \\ 0 & 0 & 1 \end{matrix}$$

Let $[E_0]=[\Lambda\phi][\Lambda\theta][\Lambda\psi]$ define the complete Eulerian rotation matrix for angles $(\phi_0, \theta_0, \psi_0)$ and $[E_0+dE]$ define the complete rotation matrix for rotations $(\phi_0+d\phi, \theta_0+d\theta, \psi_0+d\psi)$. The inverse transformation is $[E^{-1}]=[\Lambda_{-\phi}][\Lambda_{-\theta}][\Lambda_{-\psi}]$. Following this convention, the vector locating the point X" in the treatment coordinate frame after a rigid-body rotation $(d\phi, d\theta, d\psi)$ that is modeled by the rotation of hypothetical camera model 58 is given by:

$$X''=[E_0^{-1}][E_0+dE]X.$$

From this, the relationship between the space-fixed rotations $(\alpha, \beta, \gamma)$ and the body-fixed Eulerian rotations $(d\phi, d\theta, d\psi)$ is given by:

$$[E_0^{-1}][E_0+dE]=[\Lambda_\gamma][\Lambda_\beta][\Lambda_\alpha]$$

EMPIRICAL TESTS

The reduction of this method to practice has been demonstrated in the following tests. In the tests, the precision of measuring actual phantom rotations will be reported in $(\alpha, \beta, \gamma)$, while numerical simulations of rotation measurement will be reported in $(\phi, \theta, \psi)$ Eulerian angles.

In the tests, an anthropomorphic skull phantom was set up on the treatment couch, with the inferior/superior axis along the x-ray camera x-axis, as it would be for a typical patient. The phantom's anterior direction was in the positive z direction. The three axes of rotation in the test setup corresponded to the space-fixed angles $(\alpha, \beta, \gamma)$, as defined in FIG. 7. A tiltmeter measured angles $(\alpha, \beta)$ relative to gravity and was calibrated on a milling machine's rotary table. The resulting calibration was accurate to better than 0.1 degrees. The remaining translational and rotational degrees of freedom were measured mechanically and had precisions of 0.25 mm and 0.25 degrees, respectively.

The phantom was imaged in a CT study of 74 slices 3.0 mm thick, with each image having 512×512 pixels 0.49 mm on a side. The treatment room imaging system operated at 100 kV and 25 mA. The radiographs were 200×200 pixels, with each pixel 1.30 mm on a side.

The phantom was moved step-by-step through motions along and around each axis separately and in composite multi-axis rotations. At each step, the imaging system acquired radiographs and the algorithm computed the phantom position and orientation relative to the CT study. The correspondence between the measured and actual change in position was recorded for each individual degree of freedom. For each test position, the minimum value of $\chi^2$ at convergence was recorded.

Figure 10:
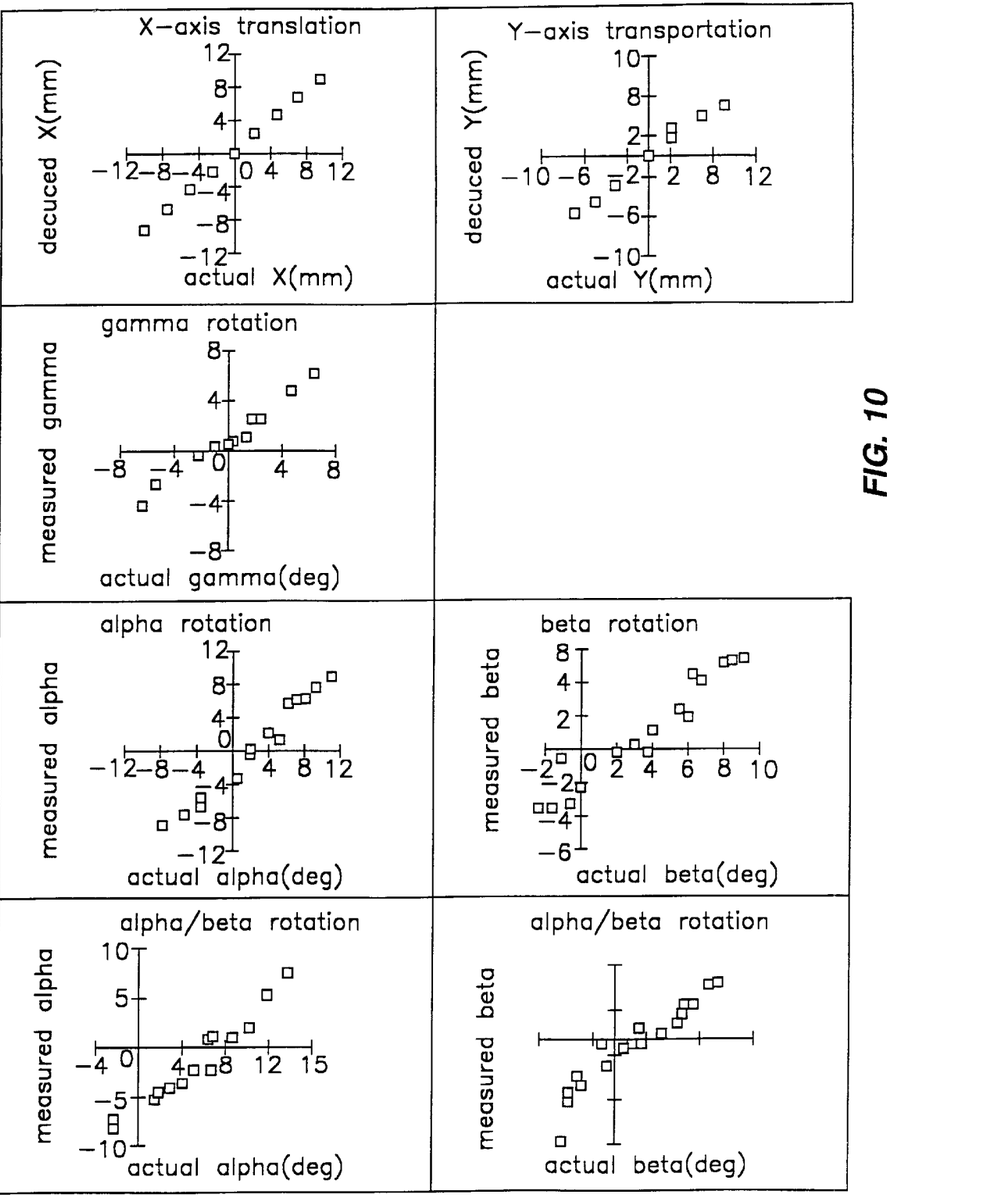
FIG. 10 contains graphs showing the empirical results for determining (x, y, z) translations, ($\alpha$, $\beta$, $\gamma$) rotations one axis at a time, and composite ($\alpha$, $\beta$) rotations for an anthropomorphic phantom.

FIG. 10 illustrates the results for determining translations and rotations empirically. This figure displays the known translations and rotations along the abscissa and the deduced translations and rotations along the ordinate. The figure shows data for rotations $(\alpha, \beta, \gamma)$ around one axis at a time, and data for composite rotations in which $\alpha$ and $\beta$ were varied simultaneously. The individual $\beta$ and $\gamma$ rotations each correspond to a composite rotation of $\phi$ and $\psi$ in the Eulerian system used to model phantom position in the DRRs. The composite rotations involved all three Eulerian angles.

Figure 11:
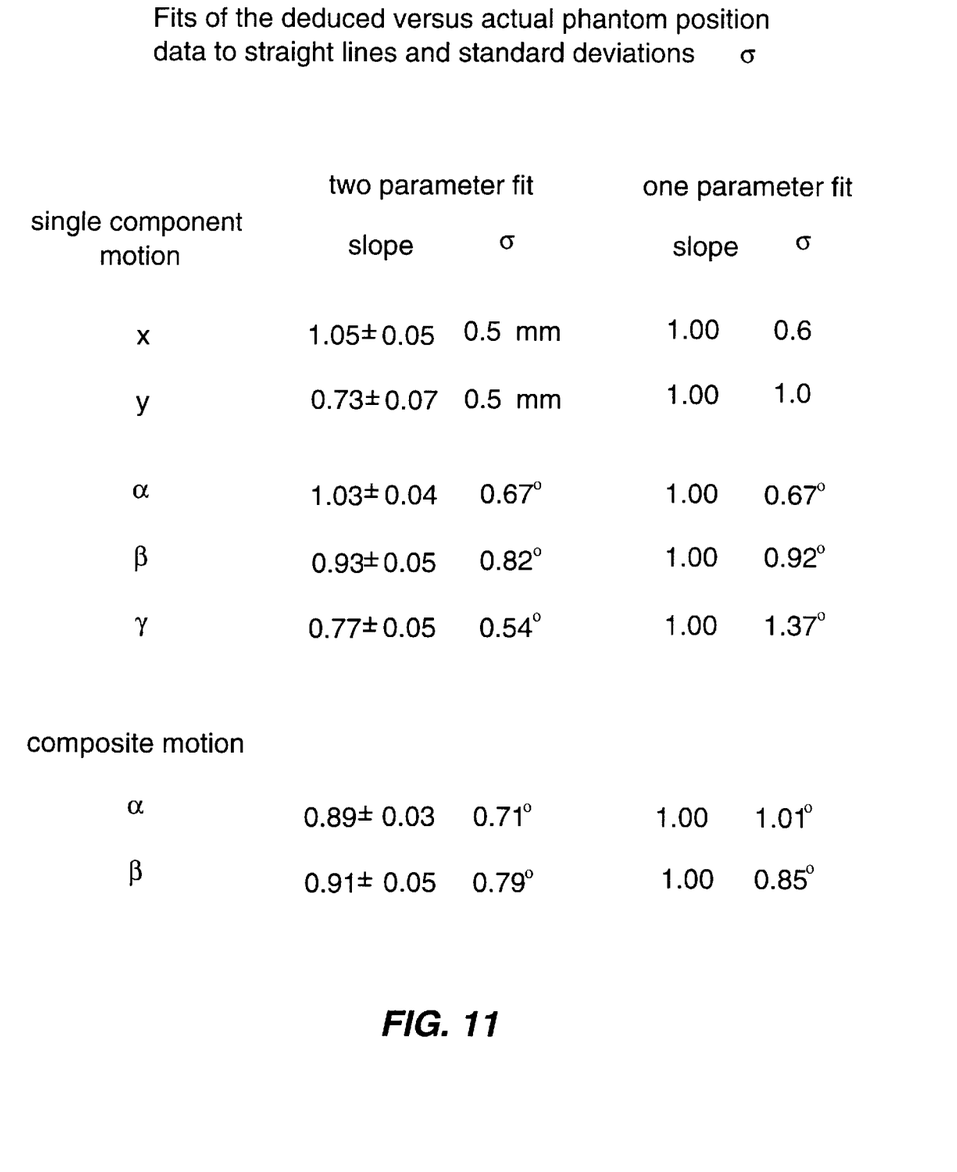
FIG. 11 is a table showing the standard deviation of errors in measuring translations and rotations of the anthropomorphic phantom.

The deduced versus actual translations and rotations should follow straight lines of slope equal to one. The data displayed in the figures were fit to straight lines, in one case fixing the slope to one, and in the other case allowing the slope to be a free parameter. The variance of the individual points about the fitted line is the standard deviation. The results of analyzing the data via straight line fits are summarized in FIG. 11.

Figure 12:
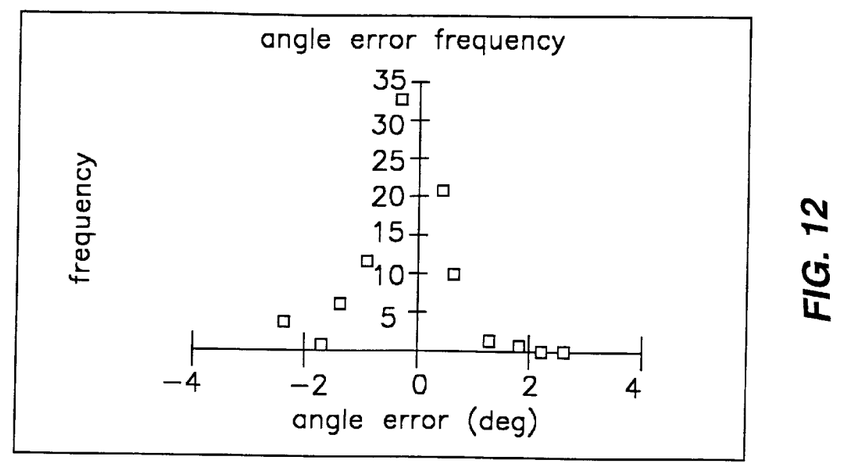
FIG. 12 is a graph illustrating the distribution of rotation measurement errors for the empirical tests. The distribution is approximately Gaussian with zero mean.
Figure 13:
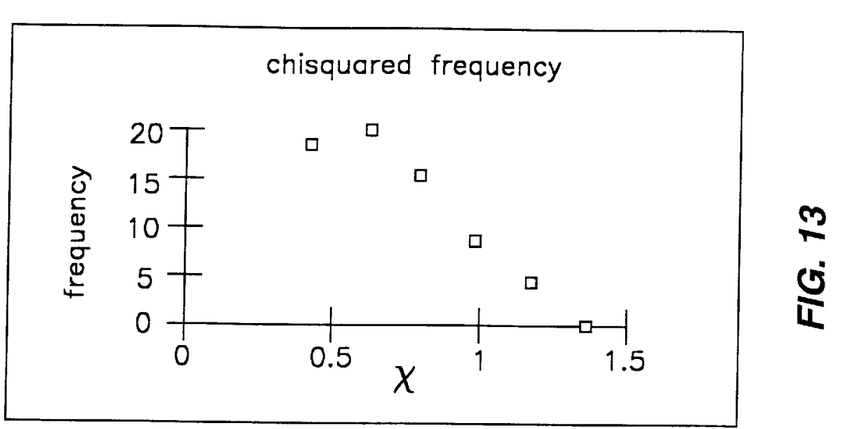
FIG. 13 is a graph showing the distribution of $\chi^2$ from the empirical tests.

FIG. 12 plots the frequency distribution of angle measurement errors. This distribution has an approximately Gaussian shape with zero mean, which is consistent with the conclusion that the process is not making systematic errors in determining the phantom position. The frequency distribution for $\chi^2$ at convergence is plotted in FIG. 13. This distribution has the basic functional form of a $\chi^2$ distribution for fits to data with randomly distributed statistical fluctuations. This again supports the conclusion that the process of extracting the image moments and edge coordinates that are fit by $\chi^2$ minimization is not making systematically biased determinations of the image features.

Figure 14:
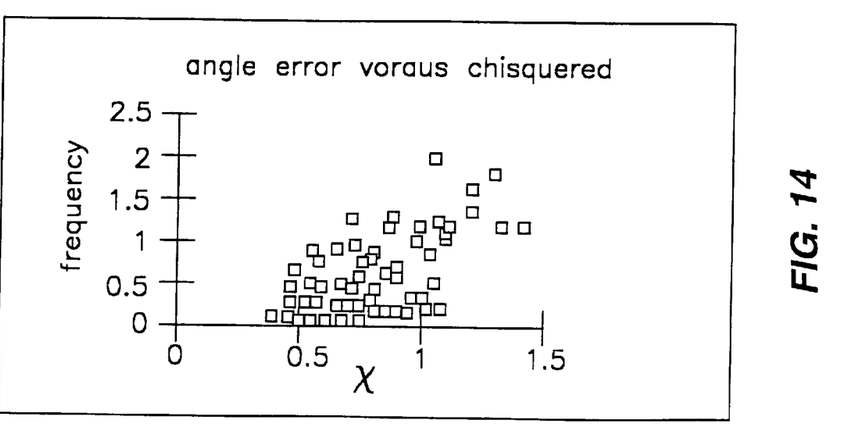
FIG. 14 is a graph showing the correlation between $\chi^2$ and the errors in angle measurements from the empirical tests.

FIG. 14 illustrates the correspondence between the measurement error for each rotational component and the value of $\chi^2$ at convergence The relationship is un-correlated for values of $\chi^2$ less than one and rotation errors less than about one degree. This is consistent with the supposition that once the position determination has gotten close, the minimization routine encounters a $\chi^2$ surface without a sharply defined minimum. Values of $\chi^2$ greater than one have a positive correlation with increasing error in the angle determinations. This is a valuable property, as it allows one to use the magnitude of $\chi^2$ to flag those rare instances where a poor determination of the patient orientation has been made.

Figure 15:
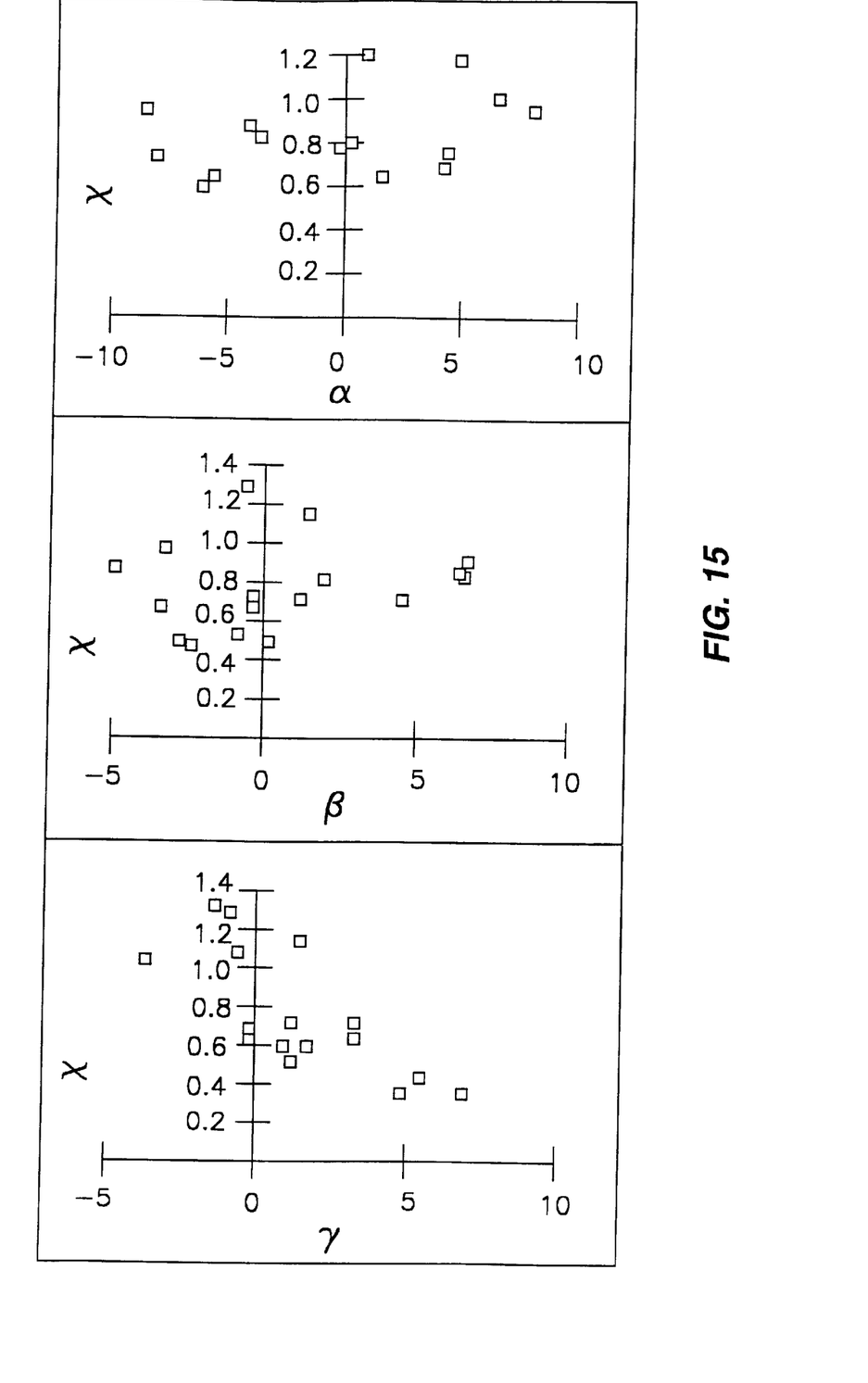
FIG. 15 is a graph showing the correlation between $\chi^2$ and the rotation angles around each axis from the empirical tests.

The correlation between $\chi^2$ and the magnitude of rotation around each axis is displayed in FIG. 15. For the $\alpha$ and $\beta$ rotations there is no apparent correlation, which indicates that the algorithm's precision and reliability is uniform over the full range of allowable orientations around these axes. The plot for the y rotations shows greater difficulty in establishing orientation in one of the two directions.

APPLICATIONS

The therapy beam alignment system and method described in the present invention can be used to direct radiation beams to any part of the body containing radiographic features. In addition, it is obvious that this method may also be used to align instruments other than radiation beams with objects other than disease regions of a patient's body. For example, this method would allow precise positioning of fabrication tools with respect to a manufactured object.

Thus, it is obvious that modifications and variations of the present invention are possible. Therefore, it is to be understood that the scope of the invention should be based on the following claims.

What is claimed is:

1. A system for aligning a plurality of radiation therapy beams with a treatment target of a patient, comprising:
   a) means of conducting a computed tomography (CT) scan;

b) means of assembling an intermediate 3-D image from said scan;

c) means of acquiring a set of at least two real images of position of said treatment target of said patient relative to a means for generating said radiation therapy beams;

d) means of producing a first feature using at least two real images;

e) means of generating a set of at least two digitally reconstructed images (DRRs) from said intermediate 3-D image;

f) means of producing a second feature vector using at least two digitally reconstructed images;

g) means of calculating a difference between said first feature vector and said second feature vector; and h) means of employing an algorithm to adjust position of said means for generating said radiation therapy beams such that said radiation therapy beams are aligned with said treatment target of said patient if said difference does not fall below a minimum allowable value.

2. The system of claim 1 comprising repeating steps b) 1–6.

3. The system of claim 1, including means of generating key pixels associated with anatomical edge features of said at least two real images and said at least two digitally reconstructed images.

4. The system of claim 3, including means of generating a mask for said at least two real images and said at least two digitally reconstructed images by highlighting said key pixels.

5. The system of claim 3, wherein said feature vectors are determined by said key pixels.

6. The system of claim 1, using a preprocessing coordinate system and a treatment coordinate system to compare position of said treatment target of said patient in said preprocessing step and in said treatment step.

7. The system of claim 6, using said preprocessing coordinate system wherein said treatment target of said patient is fixed.

8. The system of claim 6, using said treatment coordinate system wherein said treatment target of said patient is rotated and translated.

9. The system of claim 6 wherein said preprocessing coordinate system and said treatment coordinate system are related by a transformation equation.

10. The system of claim 1, allowing six degrees of freedom of position of said treatment target of said patient.

11. The system of claim 10, wherein said six degrees of freedom include translation measurements.

12. The system of claim 10, wherein said six degrees of freedom include rotational measurements.

13. The system of claim 1, wherein said difference between said vectors is determined by use of chi squared.

14. The system of claim 1, wherein said algorithm provides minimization of chi squared until convergence with said minimum allowable value.

15. The system of claim 14, including means of adjusting patient anatomy in said intermediate 3-D image.

16. The system of claim 14, including means of repositioning a camera model responsible for taking said at least two reconstructed images of said intermediate 3-D image.

17. The system of claim 16, wherein repositioning of said camera model is guided by a lookup table.

18. The system of claim 17, wherein said lookup table provides the first derivative of said translation and rotation measurements of said intermediate 3-D image.

19. The system of claim 16, wherein coordinates of repositioned said camera model are transformed into coordinates for alignment of said radiation therapy beams.

20. The system of claim 16, wherein coordinates of repositioned said camera are transformed into coordinates of alignment of said treatment target of said patient.

21. A method of aligning radiation therapy beams with a treatment target of a patient, comprising the steps of:

a) acquiring at least two current two-dimensional images indicative of a current position of said treatment target relative to a means for generating said therapy beams;

b) generating at least two reference two-dimensional images indicative of a reference position of said treatment target relative to said means for generating said therapy beams from a three-dimensional image comprising said treatment target, wherein said treatment target is aligned with said means for generating said therapy beams in said reference position;

c) comparing a current feature vector defined by said current two-dimensional images with a corresponding reference feature vector defined by said reference two-dimensional images;

d) adjusting said three-dimensional image if the difference between said current feature vector and said reference feature vector falls above a minimum allowable value; and e) applying said therapy beams if said difference between said current feature vector and said reference feature vector falls below said minimum allowable value.

22. The method of claim 21 including the step of adjusting position of said treatment target if the difference between said current feature vector and said reference feature vector falls above said minimum allowable value.

* * * * *